(12) United States Patent
Ullrich et al.

(10) Patent No.: US 8,801,710 B2
(45) Date of Patent: Aug. 12, 2014

(54) ELECTROSURGICAL SEALING TOOL HAVING HAPTIC FEEDBACK

(75) Inventors: Christopher Ullrich, Ventura, CA (US); Ali Modarres, Mont-Royal (CA); Pedro Gregorio, Verdun (CA); Cheryl Shimek, Oakland, CA (US)

(73) Assignee: Immersion Corporation, San Jose, CA (US)

( * ) Notice: Subject to any disclaimer, the term of this patent is extended or adjusted under 35 U.S.C. 154(b) by 655 days.

(21) Appl. No.: 12/962,462

(22) Filed: Dec. 7, 2010

(65) Prior Publication Data

US 2012/0143182 A1    Jun. 7, 2012

(51) Int. Cl.
*A61B 18/12* (2006.01)

(52) U.S. Cl.
USPC .............................. 606/52; 606/45

(58) Field of Classification Search
USPC .................... 606/27, 34, 41, 51–52
See application file for complete search history.

(56) References Cited

U.S. PATENT DOCUMENTS

| | | | |
|---|---|---|---|
| 3,785,381 A | 1/1974 | Lower et al. | |
| 3,950,984 A | 4/1976 | Russel | |
| 4,407,686 A | 10/1983 | Cook et al. | |
| 4,608,861 A | 9/1986 | Wachtler et al. | |
| 4,841,987 A | 6/1989 | Brown et al. | |
| 4,858,611 A | 8/1989 | Elliott | |
| 5,047,046 A | 9/1991 | Bodoia | |
| 5,188,111 A | 2/1993 | Yates et al. | |
| 5,339,799 A | 8/1994 | Kami et al. | |
| 5,357,956 A | 10/1994 | Nardella | |
| 5,389,849 A | 2/1995 | Asano et al. | |
| 5,411,511 A | 5/1995 | Hall | |
| 5,503,320 A | 4/1996 | Webster et al. | |
| 5,529,235 A | 6/1996 | Boiarski et al. | |
| 5,609,607 A | 3/1997 | Hechtenberg et al. | |
| 5,623,582 A | 4/1997 | Rosenberg | |
| 5,649,934 A | 7/1997 | Smeltzer, III et al. | |
| 5,685,474 A | 11/1997 | Seeber | |
| 5,688,270 A * | 11/1997 | Yates et al. .................. | 606/51 |

(Continued)

FOREIGN PATENT DOCUMENTS

| | | |
|---|---|---|
| CA | 2520942 | 3/2007 |
| DE | 4213426 | 10/1992 |

(Continued)

OTHER PUBLICATIONS

EP Appl. No. 11 17 6993, Extended European Search Report, dated Nov. 8, 2011.

(Continued)

*Primary Examiner* — Michael Peffley
*Assistant Examiner* — Daniel Fowler
(74) *Attorney, Agent, or Firm* — Medler Ferro PLLC

(57) ABSTRACT

A surgical tool system includes an electrosurgical tool for sealing and transecting tissue and a tactile feedback system integrated onto a handle of the tool that generates relevant feedback in at least the form of haptic effects to the user. The tactile feedback alerts the user of tissue properties, i.e., when tissue located within jaws of the tool is completely sealed, when the tissue is ready to be cut, the cutting rate or speed, the quantity of tissue located within jaws of the tool, and whether a blood vessel is fully located within jaws of tool. In addition, the tactile feedback alerts the user to the operating status of energy application during the procedure.

15 Claims, 9 Drawing Sheets

(56) References Cited

U.S. PATENT DOCUMENTS

| | | |
|---|---|---|
| 5,713,896 A | 2/1998 | Nardella |
| 5,728,044 A | 3/1998 | Shan |
| 5,733,281 A | 3/1998 | Nardella |
| 5,767,840 A | 6/1998 | Selker |
| 5,771,902 A | 6/1998 | Lee et al. |
| 5,810,880 A | 9/1998 | Jensen et al. |
| 5,833,634 A | 11/1998 | Laird et al. |
| 5,836,894 A | 11/1998 | Sarvazyan |
| 5,928,158 A | 7/1999 | Aristides |
| 5,928,159 A | 7/1999 | Eggers et al. |
| 5,950,629 A | 9/1999 | Taylor et al. |
| 5,965,880 A | 10/1999 | Wolf et al. |
| 5,989,199 A | 11/1999 | Cundari et al. |
| 6,004,335 A | 12/1999 | Kaitekunas et al. |
| 6,024,741 A | 2/2000 | Williamson et al. |
| 6,063,031 A | 5/2000 | Cundari et al. |
| 6,096,004 A | 8/2000 | Meglan et al. |
| 6,132,441 A | 10/2000 | Grace |
| 6,190,334 B1 | 2/2001 | Lasky et al. |
| 6,267,761 B1 | 7/2001 | Ryan |
| 6,354,147 B1 | 3/2002 | Gysling et al. |
| 6,375,471 B1 | 4/2002 | Wendlant et al. |
| 6,423,057 B1 | 7/2002 | He et al. |
| 6,436,107 B1 | 8/2002 | Wang et al. |
| 6,451,015 B1 * | 9/2002 | Rittman et al. ................ 606/34 |
| 6,494,882 B1 | 12/2002 | Lebouitz et al. |
| 6,594,552 B1 | 7/2003 | Nowlin et al. |
| 6,690,963 B2 | 2/2004 | Ben-Haim et al. |
| 6,718,196 B1 | 4/2004 | Mah et al. |
| 6,730,021 B2 | 5/2004 | Vassiliades, Jr. et al. |
| 6,810,281 B2 | 10/2004 | Brock et al. |
| 6,817,973 B2 | 11/2004 | Merril et al. |
| 6,945,981 B2 | 9/2005 | Donofrio et al. |
| 6,969,384 B2 | 11/2005 | de Juan, Jr. et al. |
| 7,108,695 B2 | 9/2006 | Witt et al. |
| 7,118,582 B1 | 10/2006 | Wang et al. |
| 7,122,028 B2 | 10/2006 | Looper et al. |
| 7,126,303 B2 | 10/2006 | Farritor et al. |
| 7,200,445 B1 * | 4/2007 | Dalbec et al. ................ 607/101 |
| 7,206,627 B2 | 4/2007 | Abovitz et al. |
| 7,270,664 B2 * | 9/2007 | Johnson et al. ................ 606/51 |
| 7,280,863 B2 | 10/2007 | Shachar |
| 7,300,450 B2 | 11/2007 | Vleugels et al. |
| 7,366,562 B2 | 4/2008 | Dukesherer et al. |
| 7,373,219 B2 | 5/2008 | Nowlin et al. |
| 7,393,354 B2 | 7/2008 | Buchman et al. |
| 7,422,139 B2 | 9/2008 | Shelton, IV et al. |
| 7,720,532 B2 | 5/2010 | Hashimshony et al. |
| 7,771,424 B2 | 8/2010 | McGaffigan |
| 7,963,192 B2 | 6/2011 | Mayenberger et al. |
| 8,216,212 B2 | 7/2012 | Grant et al. |
| 2001/0004700 A1 | 6/2001 | Honeycutt et al. |
| 2001/0025150 A1 | 9/2001 | de Juan, Jr. et al. |
| 2002/0112547 A1 | 8/2002 | Eltaib et al. |
| 2002/0120188 A1 | 8/2002 | Brock et al. |
| 2003/0023250 A1 | 1/2003 | Watschke et al. |
| 2003/0057973 A1 | 3/2003 | Nojima et al. |
| 2004/0009459 A1 | 1/2004 | Anderson et al. |
| 2004/0019447 A1 | 1/2004 | Shachar |
| 2004/0106916 A1 | 6/2004 | Quaid et al. |
| 2004/0167559 A1 | 8/2004 | Taylor et al. |
| 2004/0249268 A1 | 12/2004 | Da Silva |
| 2005/0021024 A1 | 1/2005 | Hooven |
| 2005/0090815 A1 | 4/2005 | Francischelli et al. |
| 2005/0131390 A1 | 6/2005 | Heinrich et al. |
| 2005/0223327 A1 | 10/2005 | Cunningham et al. |
| 2005/0245910 A1 | 11/2005 | Wright et al. |
| 2006/0030845 A1 * | 2/2006 | Leung et al. ................ 606/41 |
| 2006/0033703 A1 | 2/2006 | Olien et al. |
| 2006/0095033 A1 | 5/2006 | Garabedian et al. |
| 2006/0142657 A1 | 6/2006 | Quaid et al. |
| 2006/0206031 A1 | 9/2006 | Hasegawa |
| 2006/0207978 A1 | 9/2006 | Rizun et al. |
| 2006/0264755 A1 | 11/2006 | Maltz et al. |
| 2006/0278680 A1 | 12/2006 | Viola et al. |
| 2006/0279534 A1 | 12/2006 | Powers et al. |
| 2006/0293643 A1 | 12/2006 | Wallace et al. |
| 2007/0018958 A1 | 1/2007 | Tavakoli et al. |
| 2007/0043352 A1 * | 2/2007 | Garrison et al. ................ 606/51 |
| 2007/0062547 A1 | 3/2007 | Pappone |
| 2007/0073282 A1 | 3/2007 | McGaffigan et al. |
| 2007/0112284 A1 | 5/2007 | Hoffman et al. |
| 2007/0135735 A1 | 6/2007 | Ellis et al. |
| 2007/0142749 A1 | 6/2007 | Khatib et al. |
| 2007/0175962 A1 | 8/2007 | Shelton, IV et al. |
| 2007/0175964 A1 | 8/2007 | Shelton et al. |
| 2007/0270884 A1 | 11/2007 | Smith et al. |
| 2007/0279401 A1 | 12/2007 | Ramstein et al. |
| 2008/0009747 A1 | 1/2008 | Saadat et al. |
| 2008/0086120 A1 | 4/2008 | Mirza et al. |
| 2008/0117166 A1 | 5/2008 | Rosenberg |
| 2008/0161796 A1 | 7/2008 | Cao et al. |
| 2008/0167662 A1 | 7/2008 | Kurtz |
| 2008/0167672 A1 | 7/2008 | Giordano et al. |
| 2008/0197167 A1 | 8/2008 | Viola et al. |
| 2008/0251568 A1 * | 10/2008 | Zemlok et al. ............. 227/175.1 |
| 2008/0251569 A1 | 10/2008 | Smith et al. |
| 2009/0090763 A1 | 4/2009 | Zemlok et al. |
| 2009/0163904 A1 | 6/2009 | Miller et al. |
| 2010/0179423 A1 | 7/2010 | Ramstein et al. |
| 2011/0046659 A1 | 2/2011 | Ramstein et al. |
| 2011/0062211 A1 | 3/2011 | Ross et al. |
| 2011/0288573 A1 | 11/2011 | Yates et al. |
| 2012/0041436 A1 | 2/2012 | Ullrich et al. |
| 2012/0116379 A1 | 5/2012 | Yates et al. |
| 2012/0138658 A1 | 6/2012 | Ullrich et al. |

FOREIGN PATENT DOCUMENTS

| | | |
|---|---|---|
| EP | 1 254 637 | 11/2002 |
| EP | 2 044 890 | 4/2009 |
| EP | 2 218 409 | 8/2010 |
| EP | 2 277 458 | 1/2011 |
| EP | 2 283 781 | 2/2011 |
| EP | 2 417 925 | 2/2012 |
| WO | WO 94/24949 | 11/1994 |
| WO | WO 03/020139 | 3/2003 |
| WO | WO 03/090630 | 11/2003 |
| WO | WO 2004/067053 | 8/2004 |
| WO | WO 2005/013803 | 2/2005 |
| WO | WO 2005/110304 | 11/2005 |
| WO | 2007/067628 A1 | 6/2007 |
| WO | WO 2008/033937 | 3/2008 |
| WO | 2009/009220 A2 | 1/2009 |
| WO | 2009/009220 A3 | 1/2009 |
| WO | 2010/008663 A1 | 1/2010 |
| WO | 2010/065314 A1 | 6/2010 |
| WO | 2010/083060 A1 | 7/2010 |

OTHER PUBLICATIONS

EP Appl. No. 11 19 1549, Extended European Search Report, dated Feb. 22, 2012.

"Tactile Sensor Acts as a Human Finger in Minimally Invasive Surgery", www.physorg.com/news102155952.html, 2007.

Bethea, et al., Abstract of: "Application of Haptic Feedback to Robotic Surgery", http://www.liebertonline.com/doi/abs/10.1089/1092642041255441, Downloaded: Nov. 25, 2008.

Bholat, et al., Abstract of: "Tactile Feedback is Present During Minimally Invasive Surgery", J Am Coll Surg, Oct. 1999, 189(4), pp. 349-355; http://www.ncbi.nlm.nih.gov/pubmed/10509459, Downloaded: Nov. 25, 2008.

Hannaford, et al., "Computerized Endoscopic Surgical Grasper", Proceedings, Medicine Meets Virtual Reality, San Diego, CA, Jan. 1998.

Hu, et al., "Real-Time Haptic Feedback in Laparoscopic Tools for Use in Gastro-Intestinal Surgery", T. Dohi and R. Kikinis (Eds.): MICCAI 2002, LNCS 2488, (2002), pp. 66-74.

Marvik, et al., Abstract of: "Ergonomic Design Criteria for a Novel Laparoscopic Tool Handle with Tactile Feedback", Minerva Chirurgica ISSN 0026-4733, vol. 61, No. 5, (2006), pp. 435-444.

(56) References Cited

OTHER PUBLICATIONS

Moy, et al., Abstract of: "A Compliant Tactile Display for Teletaction", http://ieeexplore.ieee.org/xpl/freeabs_all.jsp?tp=&arnumber=845247&isnumber=18314, Downloaded: Nov. 25, 2008.

Okamura, et al., "The Haptic Scissors: Cutting in Virtual Environments", Proceedings of the 2003 IEEE International Conference on Robotics & Automation, Taipei, Taiwan, Sep. 14-19, 2003.

Schirmbeck, et al., "Tactile Feedback without Direct Touch: An Achievement for Robotically Working Heart Surgeons?", nereja.free.fr/files/BMT2005Haptic1.pdf, Downloaded: Nov. 25, 2008.

Yao, et al., "A Tactile Enhancement Instrument for Minimally Invasive Surgery", Computer Aided Surgery, vol. 10, No. 4, pp. 233-239, MICCAI (2004), pp. 89-96.

International Search Report for PCT/US2012/047006, Oct. 5, 2012.

* cited by examiner

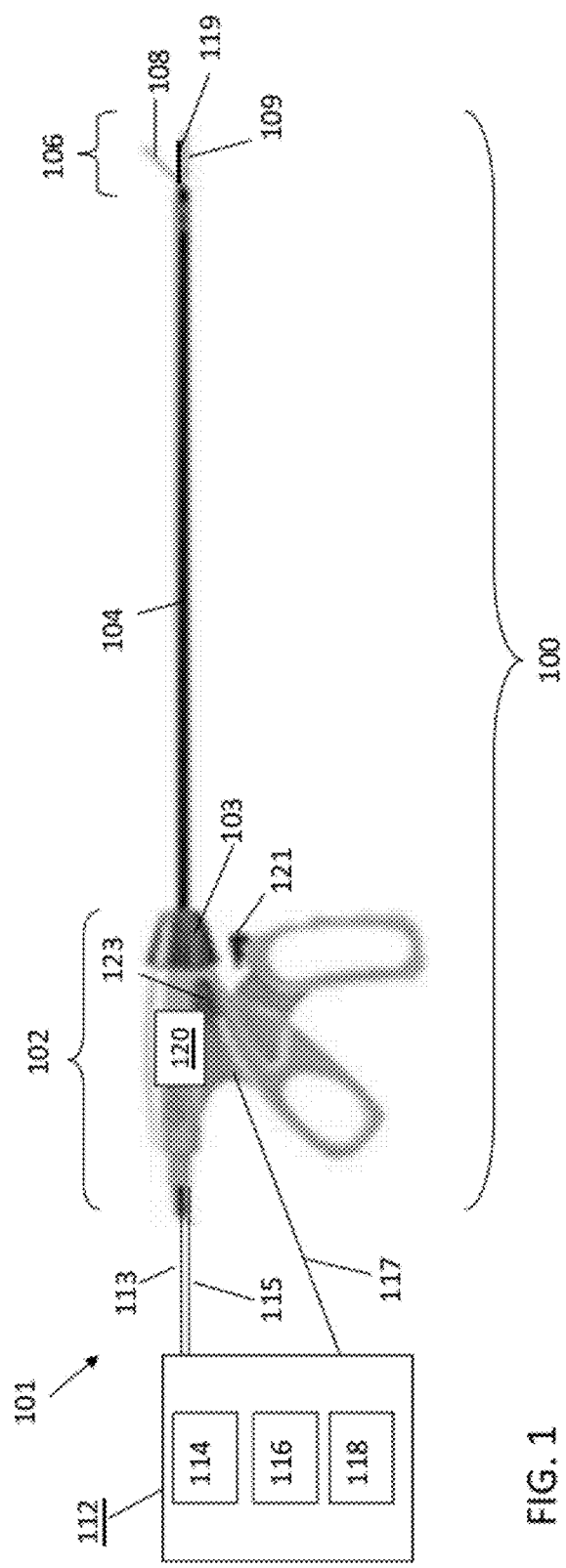
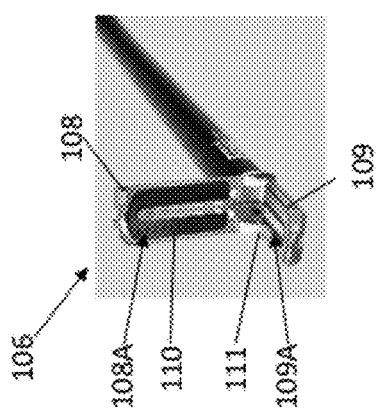
FIG. 1
FIG. 1A

ELECTROSURGICAL SEALING TOOL HAVING HAPTIC FEEDBACK

FIELD OF THE INVENTION

Embodiments hereof relate to surgical tools for treating tissue, wherein information related to the tissue treatment is processed and displayed to a user in one or more feedback modes integrated onto a handle of the tool.

BACKGROUND OF THE INVENTION

As opposed to open surgery in which a surgeon cuts a relatively large incision in the skin of a patient for accessing internal organs, minimally invasive surgical procedures are performed by making relatively small incisions and then inserting tools through the incisions to access the organs. Minimally invasive surgery usually results in shorter hospitalization times, reduced therapy requirements, less pain, less scarring, and fewer complications.

Although minimally invasive surgical procedures involving small incisions include many advantages over open surgery, minimally invasive surgery can still create challenges to a surgeon. For example, the surgeon must typically rely on a miniature camera introduced through an incision to view the patient's internal organs and see how the movement and operation of the tools affects the organs. The camera transmits images to a visual display, allowing the surgeon to see the internal organs and tissues and to see the effect of other minimally invasive tools on the organs and tissues. In this way, the surgeon is able to perform laparoscopic surgery, dissection, cauterization, endoscopy, telesurgery, and the like.

Compared to open surgery, however, minimally invasive surgery presents limitations in visual and haptic perceptions, and creates challenges unique to this type of surgery. One of the major concerns relevant to both open surgery and minimally invasive surgery is the potential for tissue damage, possibly caused by inappropriate use of force or excessive application of energy/heat. For example, electrosurgical tools operate by stimulating tissue with a high frequency electric current. The frequency of the current controls the action of the tool, which can include sealing/coagulating and/or dissecting. In both open surgery and minimally invasive surgery, the tissue being sealed is clamped within the jaws of a tissue sealing tool and is not visible to the user, and therefore direct visualization is not helpful in determining when an electrosurgical endpoint has been reached, i.e., when the clamped tissue is completely sealed. Surgeons must often rely on experience and indirect visualization to determine when the tissue is sealed, dissected or when other changes have occurred in the tissue. Based on the foregoing, there is a need for improved minimally invasive surgical tools and in particular, there is a need for minimally invasive surgical tools having improved feedback related to the surgical procedure.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a diagram illustrating a side view of a surgical tool system including a laparoscopic surgical tool and an external control system according to an embodiment hereof.

FIG. 1A is an enlarged view of the distal end of the laparoscopic surgical tool of FIG. 1.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" refer to a position distant from or in a direction away from the clinician. "Proximal" and "proximally" refer to a position near or in a direction toward the clinician.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Embodiments hereof relate to a surgical tool system 101 that includes a laparoscopic surgical tool 100 for sealing and transecting tissue, a control system 112 for providing electrosurgical energy to tool 100, and a tactile feedback system 120 integrated into tool 100 that generates relevant feedback in at least the form of haptic effects to the user. As will be explained in more detail herein, the tactile feedback provided by feedback system 120 alerts the tool user of tissue properties such as but not limited to when tissue located within the jaws of tool 100 has been completely sealed, when the tissue is ready to be cut, the cutting rate or speed, the quantity of tissue located within the jaws of tool 100, and whether a blood vessel is located within the jaws of tool 100. In addition, as will be explained in more detail herein, the tactile feedback provided by feedback system 120 may supply information relating to the operating status of tool 100 to the user such as but not limited to the presence or absence of energy application.

Figure 2:
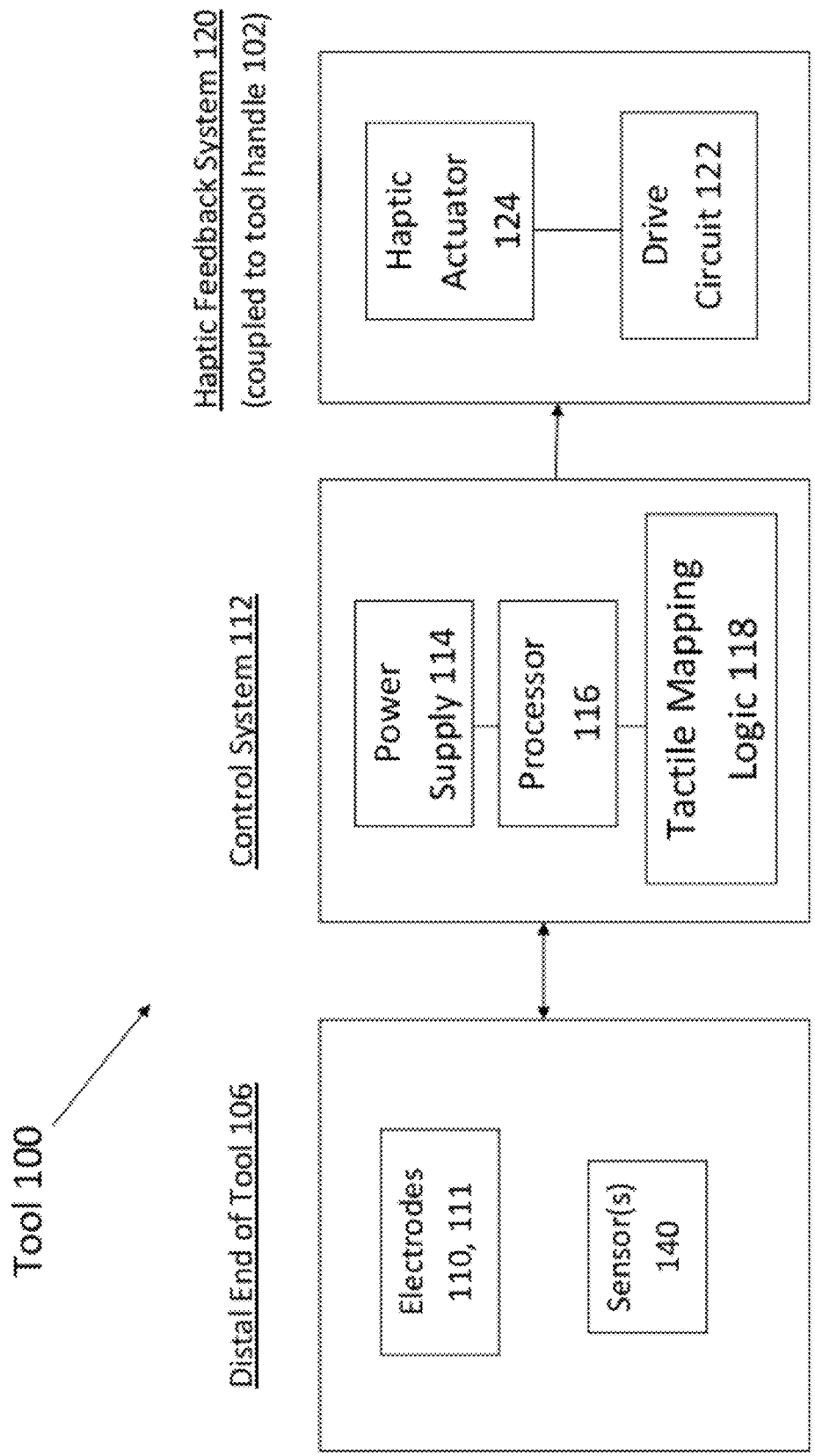
FIG. 2 is a block diagram of the surgical tool system of FIG. 1.

FIGS. 1, 1A, and 2 illustrate an embodiment of an exemplary surgical tool system 101 that includes a surgical tool or device 100 and a control system 112. In one embodiment, surgical tool 100 is a laparoscopic tool which is configured to be inserted through a trocar or other minimally invasive access port. In another embodiment (not shown), surgical tool 100 is a surgical device adapted for an open medical tissue-sealing procedure. Surgical tool 100 includes a handle 102, a shaft 104, and a distal portion 106 having jaw members 108, 109. Jaw members 108, 109 include opposed surfaces 108A, 109A, respectively, which are arranged to close toward each other and clamp or grasp tissue therebetween. Jaw members 108, 109 include channels (not shown in FIG. 1) formed therein respectively, for receiving a deployable cutting element 119 as it is advanced through jaw members 108, 109. For illustrative purposes only, cutting element 119 is shown in FIG. 1 as partially deployed within open jaw members 108, 109. As will be understood by those of ordinary skill in the art, in operation cutting element 119 is only advanced/deployed when jaw members 108, 109 are closed toward each other with tissue clamped therein. Shaft 104 is designed to connect handle 102 to distal portion 106 and to communicate mechanical and electrical actions of handle 102 to distal portion 106. More particularly, operation of handle 102 opens and closes jaw members 108, 109 through an internal mechanical connector (not shown) that runs from handle 102 to distal portion 106. According to some examples of the embodiment of FIG. 1 in which tool 100 is a laparoscopic tool, shaft 104 may be about 20 cm to 30 cm in length and distal portion 106 may be about 10 mm to 15 mm in length. In addition the shaft 104 is typically 5 mm in diameter, although tools with 3 mm, 10 mm and 12 mm diameters are also commonly used. By manipulating handle 102, an operator can insert distal portion 106 into the abdomen of the patient and control jaw members 108, 109. In one embodiment, handle 102 may include a rotatable knob 103 for rotating jaw members 108, 109 into position to grasp and clamp tissue. After tissue is positioned between the jaw members, jaw members 108, 109 are closed toward each other to clamp tissue therebetween and electrosurgical energy is applied via control system 112 to seal the clamped tissue. After coagulation of the clamped tissue occurs, the cutting element 119 may be advanced to cut the clamped tissue. In one embodiment, handle 102 may include a deployable trigger 121 for advancing cutting member 119 and a selectable on-off switch 123 for applying electrosurgical energy therethrough. Surgical tool 100 may be for example, the ENSEAL TRIO Device by Ethicon Endo-Surgery, Inc. or other laparoscopic tools suitable for sealing and transecting tissue.

More particularly, in order to seal the clamped tissue, jaw members 108, 109 include bipolar electrodes 110, 111, respectively, on a portion of surfaces 108A, 109A respectively. In one embodiment, electrodes 110, 111 are offset from each other so that they will not contact each other if tissue is thin. Control system 112 provides electrosurgical energy to electrodes 110, 111 in order to seal or coagulate tissue located between jaw members 108, 109. In one embodiment, electrodes 110, 111 are radiofrequency (RF) electrodes, control system 112 includes a radiofrequency (RF) generator, and electrodes 110, 111 apply RF energy from control system 112 to tissue. However, it should be understood by those of ordinary skill in the art that control system 112 may generate other types of energy for heating or ablating tissue including electrical energy, ultrasonic energy, cryoablation energy, etc., and in each case, electrodes 110, 111 would be a suitable corresponding component to apply the type of energy to tissue. Further, when utilized in conjunction with alternative types of energy, control system 112 may monitor suitable tissue, system, and/or operating properties to indicate when the treatment procedure is complete.

As shown, surgical tool 100 is a bipolar tool and a complete electrical circuit is formed between control system 112, electrodes 110 and 111, and the tissue extending between electrodes 110 and 111. However, as will be apparent to those of ordinary skill in the art, surgical tool 100 may be a monopolar tool including one or more electrode(s) at the distal portion of the tool and a reference electrode (i.e., skin patch electrode or grounding plate) positionable outside the patient's body (not shown). In a monopolar embodiment, current and/or voltage flows from control system 112, through the electrode at the distal portion of the tool, and into the grounding plate or reference electrode exterior to the patient. If multiple electrodes are located at the distal portion of the tool, the same current and/or voltage flows through each electrode and into the grounding plate or reference electrode exterior to the patient.

Electrodes 110, 111 are electrically connected to control system 112 via two electrically conductive leads 113, 115, respectively, that extend through at least one lumen (not shown) of shaft 104. Electrodes 110, 111 may be fixedly attached to the distal ends of the two electrically conductive leads by any suitable means. For example, the electrodes may be attached via welding, soldering, by the use of an electrically conductive adhesive, by the addition of a connecting element there between, or by another mechanical method. Although shown with two leads 113, 115 extending through shaft 104, it will be understood by those of ordinary skill in the art that two leads are only required for tools having bipolar electrodes integrated onto distal portion 106 of tool 100. Conversely in a monopolar tool, only one lead is required to run through shaft 104 for connecting control system 112 to one or more electrodes, while an external lead or ground line is connected the grounding plate or reference electrode exterior to the patient.

FIG. 2 is a block diagram of surgical tool system 101, further illustrating the relationship between the main components of surgical tool system 101. Control system 112 provides power to enable tool 100 to perform the tissue-sealing procedure and also communicates with both distal end 106 of tool 100 as well as handle 102 of tool 100 in order to provide haptic effects to the user. More particularly, control system 112 includes power source 114, a processor 116 for receiving measurements from one or more sensors 140 of tool 100 as will be described in more detail herein, and a controller or tactile mapping logic 118 configured to process sensor information from processor 116 into tactile feedback signals or commands. In one embodiment, power source 114, processor 116, and tactile mapping logic 118 are combined into an integral, external component that is separated from surgical tool 100 and is electrically connected to electrodes 110, 111 and haptic feedback system 120 via internal or external wires. Stated in another way, all of the components of control system 112 may be in the same external instrumentation unit. However, in another embodiment, power source 114, processor 116, and/or tactile mapping logic 118 may be separate external components that are electrically connected together. In yet another embodiment, one or more of power source 114, processor 116, and tactile mapping logic 118 may be mounted within or on handle 102 of surgical tool 100 and are electrically connected to electrodes 110, 111 and haptic feedback system 120 via only internal wires.

Power source 114 generates an alternating current of any suitable power level and frequency sufficient to seal/coagulate tissue. In one embodiment, power source 116 may be a RF power generator manufactured by Ethicon of Cincinnati, Ohio or by Covidien of Mansfield, Mass. which are both capable of providing a high output power with maximum output between 50 W-200 W. For example, power source 116 may generate 100 W at approximately 450 kHz for coagulation, although the frequency and power thereof may be varied during the procedure to allow for tissue specificity, etc. As described above, leads 113, 115 electrically connect power supply 114 and RF electrodes 110, 111 in order to supply RF power thereto.

As will be explained in more detail herein, sensor(s) 140 may include one or more of an impedance sensor, a force sensor, a displacement sensor, and/or a pressure sensor dependent on the desired haptic effects. Processor 116 is electrically connected to sensors 140 via one or more leads or other transmission medium (not shown). During operation of the tool, processor 116 receives data or measurements from sensor(s) 140 and accordingly processes or analyzes the sensor data/measurements as necessary in order to supply the correct type of input to tactile mapping logic 118. Processor 116 may include logic resources, such as a microprocessor, and may further include other specific sensor-dependent components required to analyze and store data/measurements from sensor(s) 140.

Processor 116 outputs the information derived from one or more sensors of tool 100 to tactile mapping logic 118 that further processes the information according to specific algorithms and operator selections. More specifically, tactile mapping logic 118 is configured to map sensed/calculated values derived from the tool sensor(s) onto tactile feedback signals or commands. Mapping may include a function or lookup table, or may include a more complex algorithm and, if necessary, a finite state machine. Tactile mapping logic 118 determines what haptic effects are to be played and the order in which the effects are played in response to the sensed/calculated values. Tactile mapping logic 118 may be a general-purpose or specific-purpose processing device or microcontroller. In one embodiment, tactile mapping logic 118 may be associated with a memory device (not shown) for storing data and/or instructions. The memory device can be any type of storage device or computer-readable medium, such as random access memory ("RAM") or read-only memory ("ROM"). The memory device stores logical instructions, commands, and/or code executed by tactile mapping logic 118. The memory device may also be located internal to control system 112, or any combination of internal and external memory. In another embodiment, logical instructions, commands, and/or code can be implemented in hardware and incorporated in tactile mapping logic 118 using discrete logic circuitry, an application specific integrated circuit ("ASIC"), a programmable gate array ("PGA"), a field programmable gate array ("FPGA"), etc., or any combination thereof. In yet another embodiment, logical instructions, commands, and/or code can be implemented in both hardware in tactile mapping logic 118 and software/firmware stored in the memory. Although described separately from processor 116, it should be understood by those of ordinary skill in the art that such functional description is for illustrative purposes only and the same instrumentation may be utilized as processor 116 and tactile mapping logic 118.

Tactile mapping logic 118 outputs control signals to haptic feedback system 120 coupled to handle 102 of tool 100 to provide feedback information to an operator when performing a procedure. The control signals are communicated via a third lead or tether 117 (see FIG. 1) that electrically connects tactile mapping logic 118 to haptic feedback system 120. A fourth lead (not shown) may also be provided between control system 112 and handle 102 to provide an isolated ground line for a low voltage actuator circuit located in handle 102, described in more detail herein.

Haptic feedback system 120 includes at least an actuator drive circuit 122 (shown in FIG. 2) which is coupled to a haptic actuator 124 (also shown as FIG. 2) for providing haptic feedback to the operator. In order to provide feedback to the operator, haptic feedback system 120 is electrically connected to control system 112. In one embodiment, in order to communicate commands from tactile mapping logic 118 to haptic actuator 124, control system 112 provides a motor voltage along lead or tether 117 to handle 102 of tool 100. As will be explained in more detail herein, haptic actuator 124 may include but is not limited to one or more vibrotactile or kinesthetic actuators that utilize any suitable instrumentation such as but not limited to a friction brake or a dynamic motor coupled to tool 100 for providing the desired haptic effects. As such, tactile mapping logic 118 outputs control signals to drive circuit 122 which includes electronic components and circuitry used to supply haptic actuator 124 with the required electrical current and voltage to cause the desired haptic effects. As mentioned above, a fourth lead (not shown) may also be provided between control system 112 and handle 102 to provide an isolated ground line for a drive circuit 122 in handle 102 such that tactile mapping logic 118 communicates with haptic feedback system 120 via an isolated DC voltage line having two conductors.

Haptic feedback may be generated and provided to the user, including vibrotactile, kinesthetic, handle deformation and/or other types of tactile feedback such as texture and heat. Haptic actuators 124 may include electromagnetic motors, eccentric rotating mass ("ERM") actuators in which an eccentric mass is moved by a motor, linear resonant actuators ("LRAs") in which a mass attached to a spring is driven back and forth, shape memory alloys, electro-active polymers that deform in response to signals, mechanisms for changing stiffness, vibrotactile actuators, inertial actuators, piezoelectric actuators, or other suitable types of actuating devices. In one embodiment, haptic actuator 124 can be implemented as an inertial actuator to provide vibrotactile feedback to the operator. In another embodiment, kinesthetic haptic feedback may utilize, for example, solenoids to change the stiffness/damping of handle 102, small air bags that change size in handle 102, or shape changing materials. A detailed description of drive circuits and haptic actuators suitable for use herein may be found in U.S. patent application Ser. No. 11/862,639, filed Sep. 28, 2007, herein incorporated by reference in its entirety.

In one embodiment, haptic actuator 124 is a vibrotactile device that generates vibrations on handle 102 for haptic feedback. For example, in one embodiment, one or more vibrotactile actuators may be incorporated in handle 102 at several locations corresponding to the fingers and thumb of a hand of the surgeon for providing high bandwidth vibrotactile feedback over the entire handle. A target acceleration of between 4-5 G's at resonance is desirable, along with response greater than 2.5 G's from 100-250 Hz. In one embodiment, all moving mass components relating to actuation of haptic actuator 124 are internal to tool 100.

In another embodiment, haptic actuator 124 is a kinesthetic device such as a friction brake or a motor that enables variable resistance to motion, lock-out, barrier and detent display on handle 102 for haptic feedback. For example, in one embodiment, trigger 121 for cutting element 119 may be fitted with a kinesthetic actuation means to enable kinesthetic haptic effects. In addition, one or more kinesthetic actuators may be incorporated in handle 102 at several locations corresponding to the fingers and thumb of a hand of the surgeon for providing resistance of motion to the entire grasper portion of the handle. The kinesthetic actuators must be capable of at least significantly impeding motion. For example, in one embodiment, the kinesthetic actuators may have a resistance of between 20% and 30% of the maximum applied force in order to display effective impeding forces. In another embodiment, the kinesthetic actuators may be capable of impeding all user motion to communicate a "lock-out" mode.

As previously mentioned, the type of tool sensor(s) as well as the operation of processor 116 depends on desired haptic effects. In one embodiment, the sensor is an impedance sensor and the processor continuously measures impedance of the tissue clamped between jaws 108, 109 of tool 100 to provide an indication of when the tissue-sealing cycle or treatment is complete. Specifically, electrosurgical energy aims to seal cells at a treatment site while leaving the basic structure of the tissue intact. It is essential for the user to know when the sealing cycle is complete because the user should not cut the tissue prior to adequate sealing. Although some sealing tools include a predetermined audible alert at the end of a predetermined amount of time that is assumed to be the end of the sealing cycle (i.e., fifteen seconds), audible alerts are easily confused with other audible alerts and may not be heard in noisy operating room environments. In addition, the use of time alone is not a good indication of seal quality. Real-time impedance measurement permits the user to gauge the completeness, i.e., degree of tissue sealing, of the coagulation treatment. Sealed tissue blocks electrical signals, which may be accurately indicated by simultaneously monitoring the impedance of tissue. Accordingly, impedance may be monitored to indicate when tissue sealing is complete and haptic effects may be provided to the handle of the tool to alert that user that the sealing cycle is complete.

Figure 3:
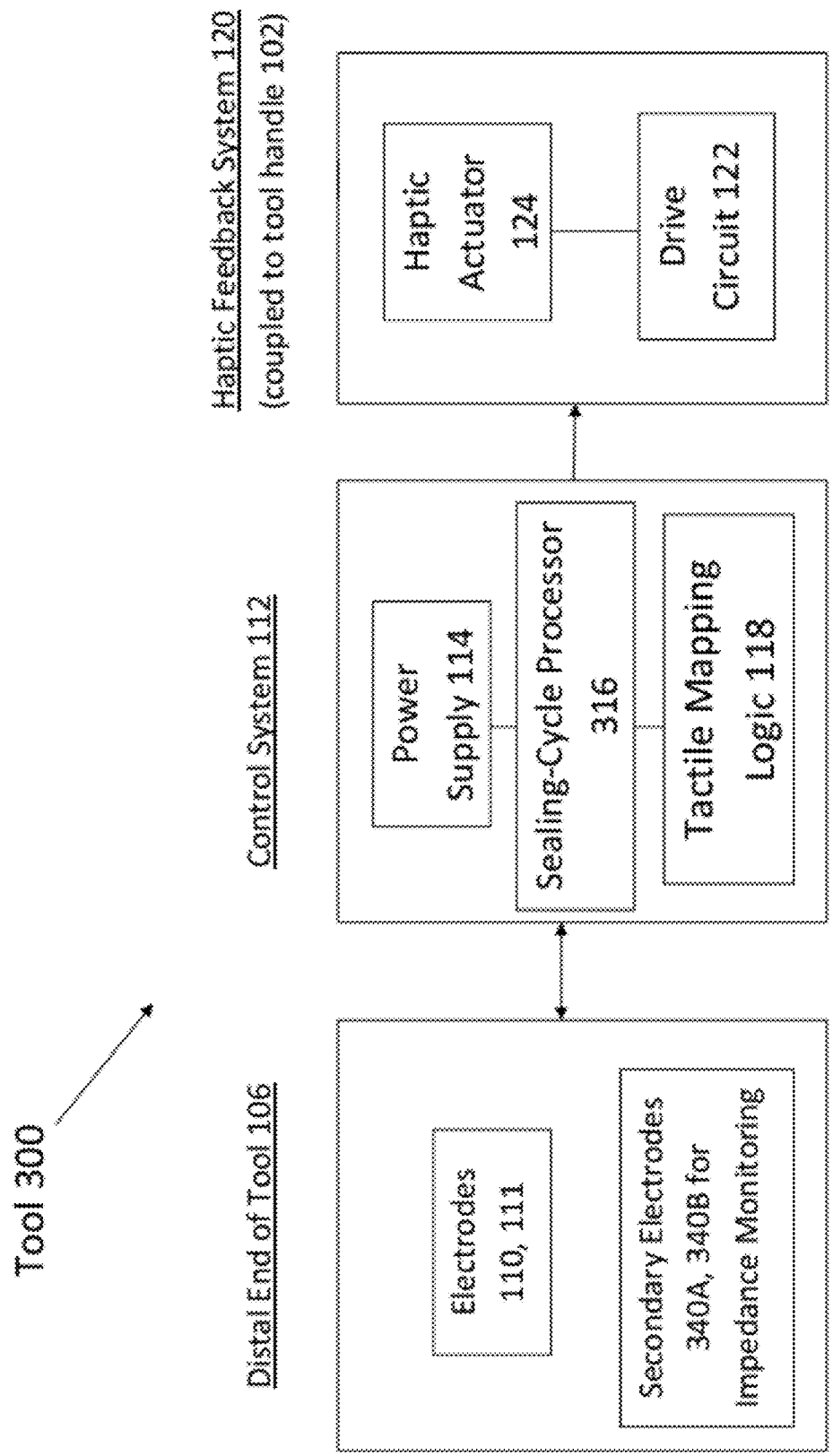
FIG. 3 is a block diagram of a surgical tool system according to an embodiment hereof in which haptic effects relating to the completeness of tissue-sealing cycle are communicated to the user.

More particularly, as shown in FIG. 3, surgical tool 300 includes a secondary pair of electrodes 340A and 340B which are capable of measuring tissue impedance and the control system includes sealing-cycle processor 316. Electrodes 340A, 340B may be located on opposed surfaces 108A, 109A of jaw members 108, 109, respectively, adjacent electrodes 110, 111. Electrode 340A is electrically connected to power source 114 via a lead (not shown), and electrode 340B is electrically connected to sealing-cycle processor 316 via a lead (not shown). Power source 114 and sealing-cycle processor 316 work together in order to continuously measure impedance of the target tissue in real time. Power source 114 is capable of generating a harmless alternating current in the range of 1 kHz to 500 kHz or other suitable frequencies known to those of skill in the art of bioelectric impedance to allow for the measurement of impedance. For example, a current of 2 microamperes at 50 KHz may be used. While current is flowing, sealing-cycle processor 316 measures a corresponding resistance between electrodes 340A, 340B. Sealing-cycle processor 316 then arithmetically converts the resistance to an impedance measurement. In order to measure impedance, sealing-cycle processor 316 may include logic resources, such as a microprocessor, a voltage-current converting circuit, an amplifying circuit, an A/D converting circuit, and an impedance arithmetic operation section. In order to determine adequate tissue sealing, sealing-cycle processor 316 may record and/or calculate various parameters including current, voltage, power, impedance, and rates of change of these parameters. Although described herein as measuring impedance via secondary pair of electrodes 340A, 340B, it will be understood by those of ordinary skill in the art that the configuration of tool 100 may be adjusted such that impedance is alternatively monitored between electrodes 110, 111, thus eliminating the need for the secondary pair of electrodes.

When impedance or other measured/calculated system parameter(s) signifies that tissue sealing is complete, tactile feedback system 120 provides haptic effects to the user. The completion of the tissue-sealing cycle needs to be indicated to the user to enable them to proceed with the surgery. In one embodiment, the haptic effects may be a single haptic alert such as a vibrotactile alert to indicate completion of the tissue-sealing cycle. In another embodiment, the haptic effects may include continuous feedback based on live impedance values as the tissue impedance approaches completion of the tissue-sealing cycle such as a vibrotactile feedback with a sequence of increasing amplitudes and/or a kinesthetic barrier or resistance on trigger 121 of handle 102. It will be understood by those of ordinary skill in the art that haptic effects may include both alerts and continuous feedback, and may include both vibrotactile and kinesthetic effects.

Monitoring impedance at or adjacent to the treatment site and determining completeness of the treatment can be determined according to any criteria. For example, adequate tissue sealing may be determined via the detection of a particular value of electrical impedance (i.e., when impedance reaches 450 ohms, the tissue is assumed to be sealed) or via the detection of a series of impedance measurements that are relatively constant over a desired period of time or over a defined number of successive impedance measurements. In one embodiment, a complete tissue seal may be associated with an impedance change of 10 ohms. A lookup or function table may be utilized to map sensed/calculated impedance values onto tactile feedback signals or commands to provide increasing feedback to the surgeon as tissue sealing occurs. Other lookup functions are possible and may be user-selectable. In another embodiment, a complete tissue seal may be a function of various observed quantities such as impedance, impedance change, current, voltage, power, and the like or may be mapped from the output of a tissue model.

In one embodiment, application of energy for sealing tissue continues for a predetermined time period that is assumed to be the end of the sealing cycle. For example, the application of energy may occur for a sealing cycle of fifteen seconds. A negative valence vibrotactile alert may be provided at the end of the predetermined time period if the impedance information does not indicate that sealing is complete, and a positive valence vibrotactile alert may be provided at the end of the predetermined time period if the impedance information indicates that sealing is complete. Accordingly, the user may utilize the haptic alert when deciding whether an additional sealing cycle needs to be applied to the target site in order to completely seal the tissue.

In yet another embodiment, tactile mapping logic 118 may output command signals to power source 114. For example, when the impedance of the tissue indicates that tissue sealing is complete, tactile mapping logic 118 may output a command signal to shut down power source 114, thereby preventing delivery of additional energy to the tissue and controlling the behavior of tool 100.

Figure 4:
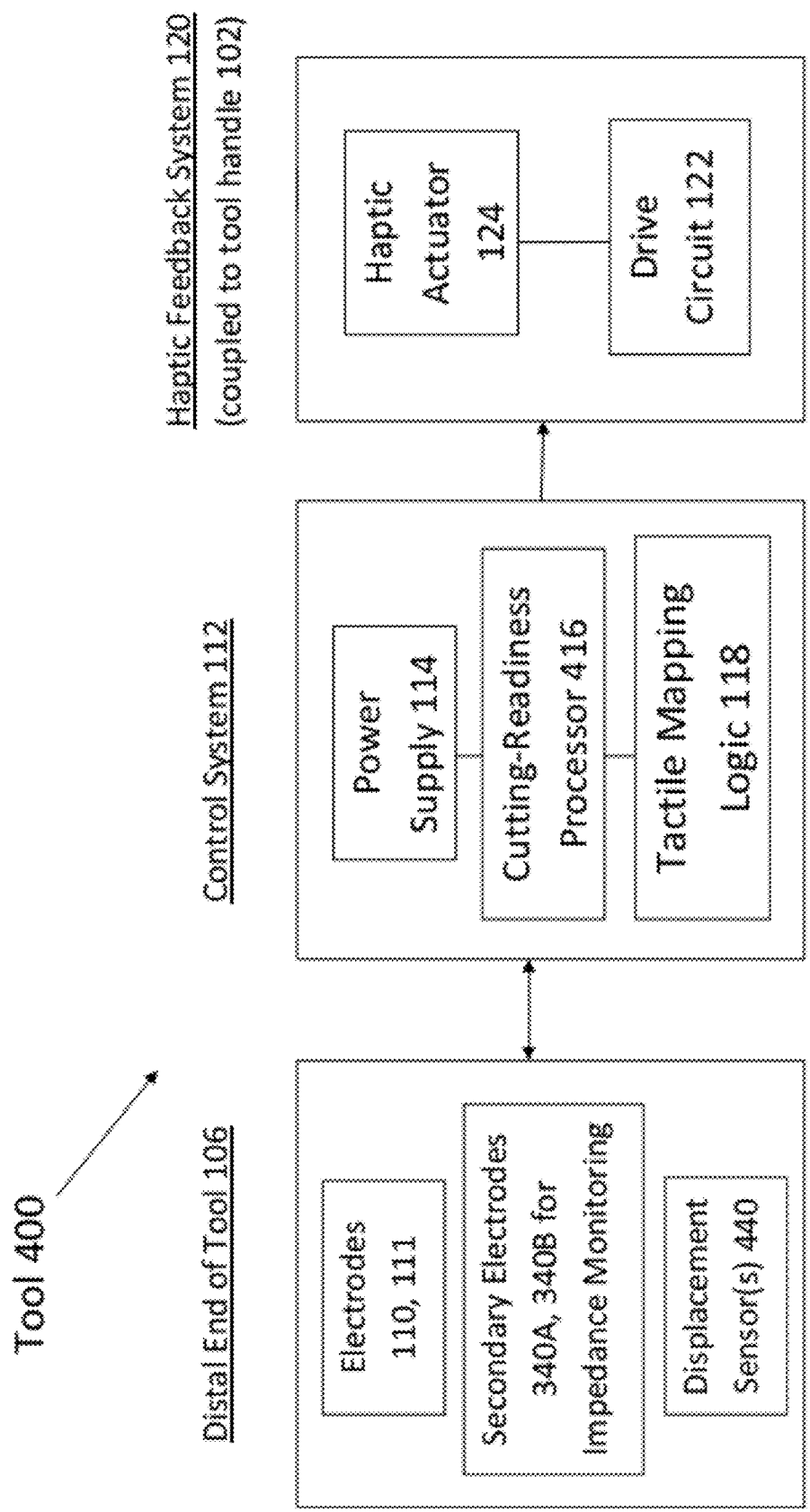
FIG. 4 is a block diagram of a surgical tool system according to an embodiment hereof in which haptic effects relating to cutting-readiness are communicated to the user.

In another embodiment shown in FIG. 4, the impedance measurements may be utilized to provide feedback related to cutting readiness and/or rate. Laparoscopic sealing tools may rely on the operator to control advancement of the cutting element during the sealing process. In addition to performing dissection, cutting element 119 also plays an important role in the sealing portion of the procedure because blade advancement controls the compression force exerted on the tissue clamped between the jaws of the tool. Adequate compression is critical in achieving complete sealing, especially with thick tissue and/or blood vessels. Thus, the user often wants to advance the cutting element just proximal to tissue to achieve maximum compression for sealing the tissue, but wants to defer advancement of the cutting element into the tissue until it is adequately sealed. A cutting-readiness processor 416 makes impedance or other electrical parameter calculations that may be utilized to provide the user with guidance as to the readiness of tissue for cutting and as to the appropriate rate or speed of cutting. In order to assure adequate tissue sealing, it is important to limit or control advancement of the cutting element and therefore feedback as to the appropriate cutting speed is useful. As shown in FIG. 4, in this embodiment tool 400 includes secondary pair of electrodes 340A and 340B for monitoring impedance, a displacement sensor 440 which is capable of measuring displacement of cutting element 119, and a cutting-readiness processor 416. Displacement sensor 440 is coupled to cutting element 119 to provide information relating to the position of cutting element 119, and electrodes 340A, 340B, and displacement sensor 440 are all electrically connected to cutting-readiness processor 416 via one or more leads (not shown). Jaw displacement may be measured with a potentiometer or other suitable position encoder on the hinge of the jaw members. Displacement sensor 440 continuously monitors the position of cutting element 119 to provide information to processor 416 regarding when cutting element 119 is located just proximal to the tissue such that further advancement thereof would result in cutting of the tissue, i.e., when cutting element 119 is in the cutting position. Cutting-readiness processor 416 also continuously receives impedance measurements from electrodes 340A, 340B and calculates impedance as described above with respect to processor 316.

Based on the displacement measurements from sensor 440 and the impedance measurements from electrodes 340A, 340B, cutting-readiness and/or cutting speed feedback may be provided to the user. Cutting feedback may be provided in different modes such as a training mode and an experienced mode in order to accommodate the needs of users having varying degrees of experience with the tool. In the training mode, haptic effects may include continuous active resistance feedback on trigger 121 of handle 102 based on live impedance values in order to prevent premature and/or too rapid cutting. For example, after the measurements from displacement sensor 440 indicate that cutting element 119 is in the cutting position, maximum resistance will be provided during impedance values less than 100 ohms and zero resistance will be provided for impedance values greater than 450 ohms. During impedance values between 100 and 450 ohms, the resistance on trigger 121 will gradually decrease in a continuous or stepwise fashion from maximum to zero. In experienced mode, haptic effects may include a relatively small detent on trigger 121 of handle 102 at the beginning of the cutting portion of the stroke if the measurements from displacement sensor 440 indicate that cutting element 119 is in the cutting position and the impedance is less than 450 ohms. In addition, experienced mode may include continuous vibrotactile feedback with a sequence of increasing amplitudes for impedance values between 100 and 450 ohms. In another embodiment, the amplitude of the detents is a function of the tissue impedance, so that a rough texture or sequence of barriers is present when the tissue is in a low impedance state and is progressively reduced as tissue impedance rises. This feedback may be displayed in a continuous time fashion or only during motion of the cutting element.

In addition to haptic effects relating to cutting-readiness and/or cutting rate, haptic feedback relating to the type of tissue being cut may also be provided during the cutting procedure. For example, passive kinesthetic resistance may be provided on trigger 121 and/or on handle 102 at several locations corresponding to the fingers and thumb of a hand of the surgeon. The kinesthetic resistance during motion of cutting element 119 may be a function of sensed tissue properties. For example, the kinesthetic resistance may be varied according to stiffness of the tissue being cut, which may be sensed via a strain gauge or other suitable sensor at the distal tip of the tool. A more detailed description of monitoring tissue properties such as stiffness and providing haptic effects relating thereto may be found in U.S. patent application Ser. No. 11/955,563, filed Dec. 13, 2007, herein incorporated by reference in its entirety.

Figure 5:
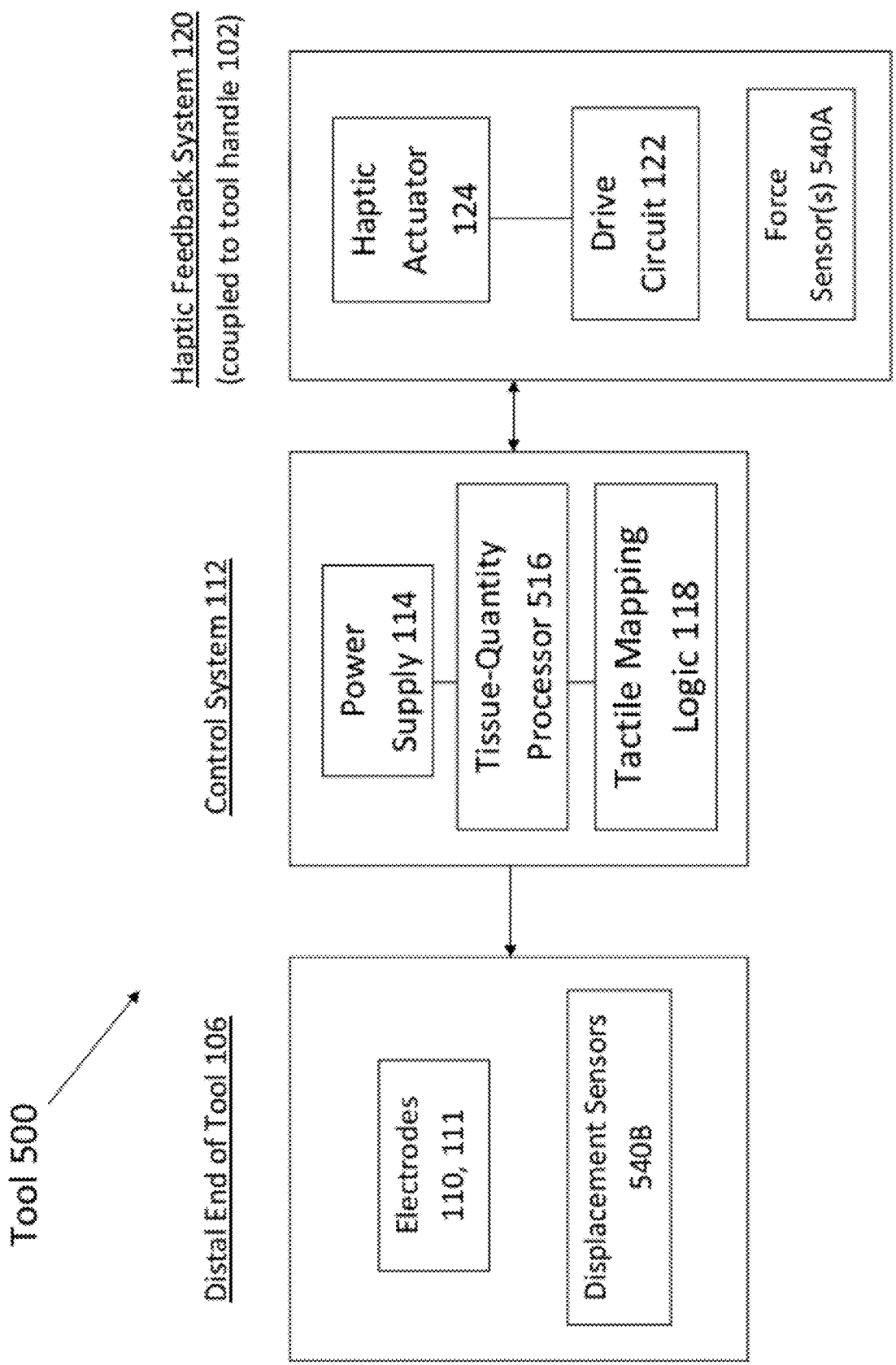
FIG. 5 is a block diagram of a surgical tool system according to an embodiment hereof in which haptic effects relating to the quantity or thickness of tissue within the jaws of the surgical tool are communicated to the user.
Figure 6:
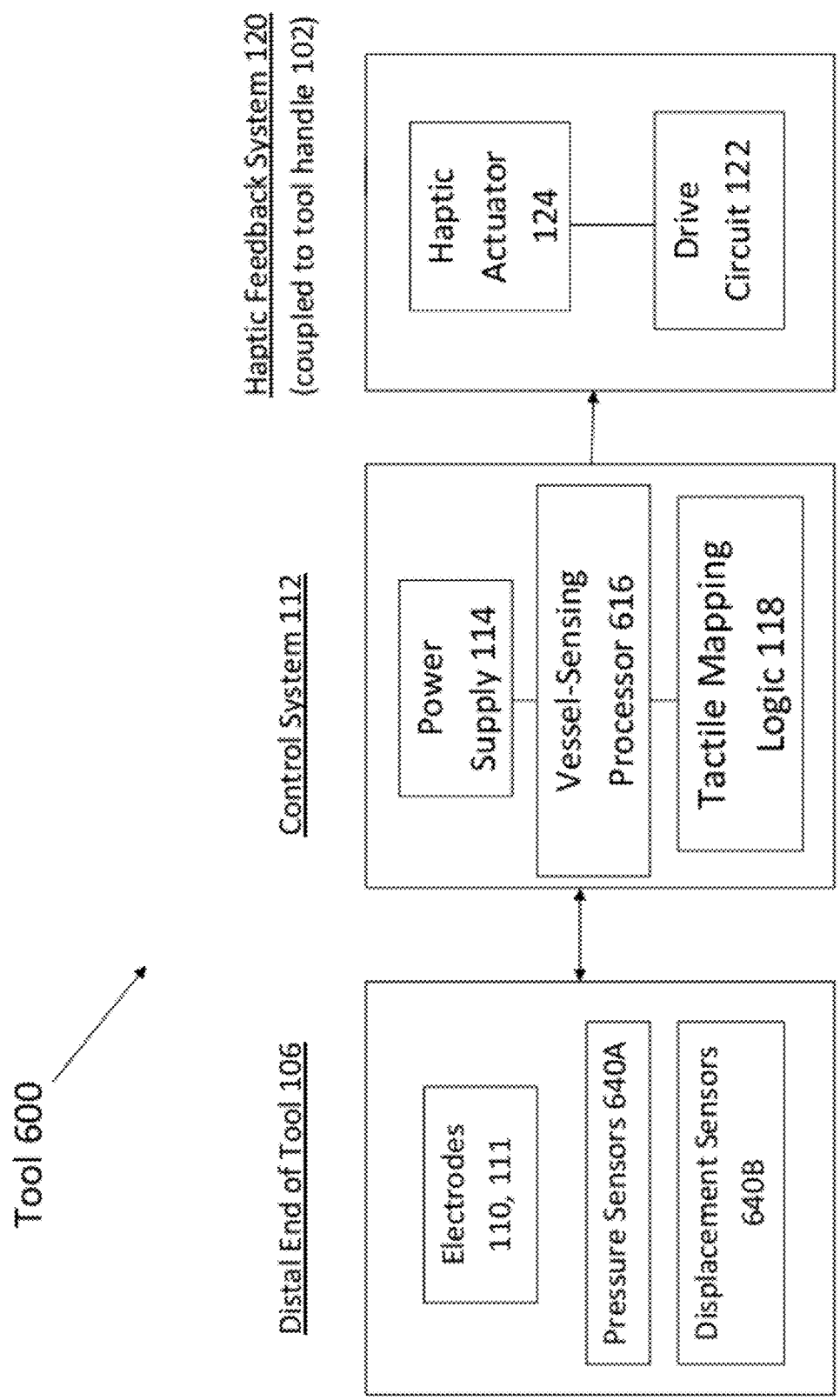
FIG. 6 is a block diagram of a surgical tool system according to an embodiment hereof in which haptic effects relating to vessel-sensing within the jaws of the surgical tool are communicated to the user.

In another embodiment shown in FIG. 5, tactile feedback system 120 alerts the tool user of the quantity of tissue located within the jaws of tool 100 to alert the user if too much tissue is being sealed. Sealing tools are typically rated for a maximum tissue and/or blood vessel thickness and users should be alerted when the amount of tissue clamped within jaw members 108, 109 exceeds this limit. In addition, the quantity of tissue in the jaws affects the quality of the seal. Tool 500 includes at least a force sensor 540A coupled to handle 102 of tool 500 and a tissue-quantity processor 516 in the control system. Force sensor 540A may be any type of force sensor that is capable of measuring the force exerted by the user to close the grasper handle of tool 500, such as a foil strain gauge, piezo strain gauge, force sensing resistor, a pressure transducer, or other suitable sensor. Exemplary products that may be utilized for force sensor 540A include Tekscan force sensing resistors and Omega foil strain gauges. Tool 500 may also include a displacement sensor 540B coupled to the distal end of the tool for monitoring the space between the jaw members. Jaw displacement may be measured with a potentiometer or other suitable position encoder on the hinge of the jaw members or the shaft of the tool. Displacement sensor 540B may be used to complement signals from force sensor 540A because high force signals when the jaw members are nearly closed is less significant than high force signals when the jaw members are just beginning to close. Thus, in one embodiment, force sensor 540A and displacement sensor 540B are utilized in conjunction to determine when an excessive amount of tissue is located within the jaw members. Tissue-quantity processor 516 continuously monitors force measurements received from force sensor 540A and displacement sensor 540B, if present, and calculates/estimates the amount of tissue located within the jaws of tool 500 from the force measurements. In one embodiment, the best indicator of tissue thickness, and thus the parameter monitored by tissue-quantity processor 516, is the rate of change of force with respect to jaw gap displacement. In addition, in one embodiment, the user may input a force state (i.e., high, medium, low) into a graphic user interface so that the calculations performed by processor 516 are consistent with the level/type of tissue that it being grasped by the tool.

Based on the force measurements from sensor 540, tissue quantity/thickness feedback may be provided to the user. Haptic feedback will be provided to users as force measurements pass through several thresholds. For example, in order to warn the user that there might be too much tissue in the jaws, the feedback may include vibrotactile alerts of increasing amplitude as the force measurements pass through the thresholds and/or kinesthetic feedback of increasing magnitude on the graspers of handle 102 as the force measurements pass through the thresholds. In another embodiment, a negative valence vibrotactile alert may be given if the amount of tissue within the device is outside of the device specification range, and a positive valence vibrotactile alert may be given if the amount of tissue within the device is within the device specification range. In addition, haptic feedback may be provided in different modes such as a training mode and an experienced mode in order to accommodate the needs of users having varying degrees of experience with the tool. In the training or beginner mode when the force exceeds a present maximum force (i.e., 4500 mNm), haptic effects may include a kinesthetic lock on trigger 121 to prevent cutting of the tissue and/or the graspers of handle 102 to prevent the user from clamping down onto the tissue. In addition, a pulsing vibrotactile alert or error may be communicated to the user. In the experienced mode when the force exceeds a present maximum force (i.e., 4500 mNm), haptic effects may include a negative valence vibrotactile alert if the user begins to cut and/or a high-magnitude kinesthetic barrier on trigger 121.

In yet another embodiment, tactile feedback system 120 alerts the tool user of the orientation of vascular tissue located within the jaws of the surgical tool. The user is notified if there are vascular structures beyond a threshold diameter within the jaws, and more importantly, the user is notified if there is vascular tissue that is not completely within the jaws or not well oriented in the jaws. Tool 600 includes one or more pressure sensors 640A and one or more displacement sensors 640B coupled to the distal end 106 of the tool, and a vessel-sensing processor 616 in the control system. Jaw displacement may be measured with a potentiometer or other suitable position encoder on the hinge of the jaw members. Pressure sensing is most effectively achieved with a capacitive pressure sensor array such as those made by Pressure Profile Systems. In one embodiment, an array of microsensors is coupled to the distal end 106 of the tool for sensing pressure and displacement of the jaw members. Vessel-sensing processor 616 continuously monitors pressure and displacement measurements received from sensors 640A, 640B, respectively, and interprets pressure/pulsation data to determine if a blood vessel extends beyond distal tip of device. Detailed description of possibly suitable sensors and methods for detection of a blood vessel with a minimally invasive tool suitable for use herein may be found in U.S. Patent Publication 2010/0179423, filed Jan. 15, 2009; U.S. Patent Publication 2010/0137845, filed Dec. 3, 2008; U.S. Patent Publication 2010/0152586, filed Dec. 12, 2008; U.S. Patent Publication 2010/0179587, filed Jan. 15, 2009, each of which is herein incorporated by reference in its entirety. Haptic feedback for vessel-sensing may include both vibrotactile and kinesthetic effects. For example, in order to warn a user that a blood vessel is only partially within the jaws of tool 600, haptic effects may include a kinesthetic lock on trigger 121 to prevent cutting of the tissue and/or the graspers of handle 102 to prevent the user from clamping down onto the tissue or engaging the cutting member. In addition, a pulsing vibrotactile alert or error may be communicated to the user.

In another embodiment, pressure sensors 640A, displacement sensors 640B, and vessel-sensing processor 616 may also be utilized to alert the tool user of whether the sealing process has successfully sealed the tissue located within the jaws of the surgical tool. It is essential for the user to know if the tissue has been sealed by the electrosurgical process because the user should not release the clamped tissue from the jaws of the surgical tool prior to adequate sealing. Detection of adequate sealing can prevent a catastrophic bleed which can occur if a less than adequately sealed vessel is unclamped. More particularly, vessel-sensing processor 616 may utilize measurement signals from pressure sensor(s) 640A and displacement sensor(s) 640B to determine if vessel pulsatility, i.e., a patent lumen, still exists on both sides of the seal prior to releasing the clamped tissue. If tissue is sealed after the electrosurgical process is completed, there is no blood flow/pulsation through the blood vessel. Haptic feedback for sealing completeness may include both vibrotactile and kinesthetic effects. For example, in order to warn a user that the tissue is not completely sealed, haptic effects may include a kinesthetic lock-out or high-magnitude barrier on trigger 121 to prevent cutting of the tissue. In another embodiment, a negative valence vibrotactile alert may be given if the tissue is not completely sealed.

Figure 7:
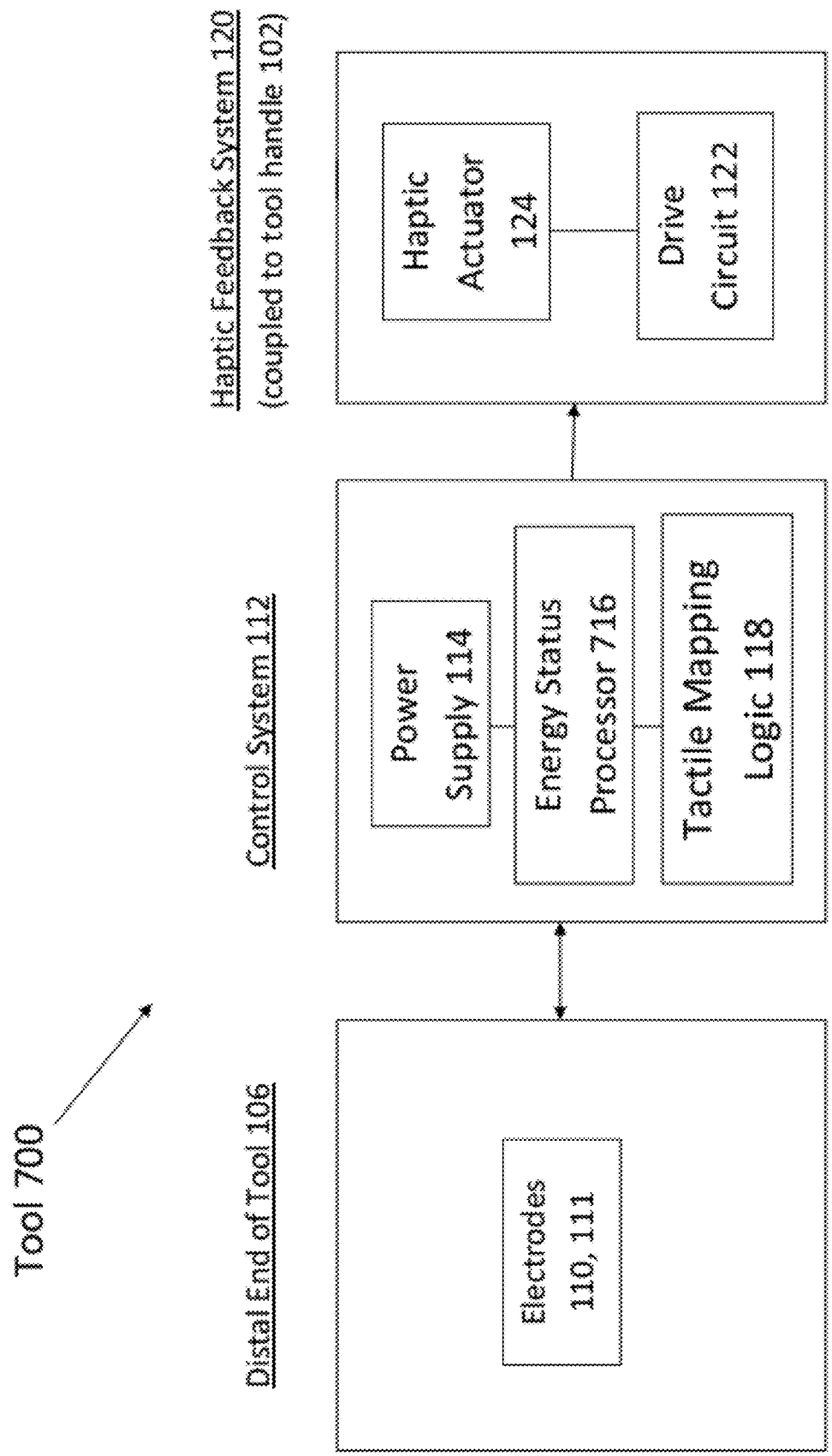
FIG. 7 is a block diagram of a surgical tool system according to an embodiment hereof in which haptic effects relating to the status of energy application are communicated to the user.

Another area in which haptic feedback is useful for the user includes various operating conditions of control system 112 and/or tool 100. In another embodiment of surgical tool 700 shown in FIG. 7, tactile feedback system 120 supplies information relating to the operating status of power source 114 to the user, i.e., to indicate when electrosurgical energy is being applied through the tool. Generators used with sealing tools such as those described herein are required to provide at least an audible alert when electrosurgical energy is activated on the sealing tool. However in noisy operating room environments, the audible indicator is not necessarily clearly communicated to the user. In this embodiment, switch 123 for applying electrosurgical energy is instrumented to enable an energy-status processor 716 to monitor the operating state thereof. When energy is enabled and switch 123 is in the "on" position, the user feels a haptic effect such as a subtle, transformer-type vibratory hum or sensation to indicate that there is energy flowing in tool 700. In addition, a kinesthetic mechanical detent may be felt by the user when energy is enabled. A pulsing vibrotactile alert or error may be communicated to the user if energy is halted during cutting. In addition, vibrotactile alerts may be utilized in conjunction with the audio alerts provided by the generator, and a distinct vibrotactile alert of higher amplitude or frequency may be utilized when a predetermined amount of time such as fifteen seconds is approaching and/or reached. This predetermined amount of time may correspond to an average or estimated time required for complete tissue sealing to occur.

Embodiments described above relate to various conditions that may be monitored and communicated to the user in the form of haptic effects. Although haptic effects for impedance monitoring, cutting-readiness, tissue-quantity, vessel-sensing, and energy-status are each described separately herein, it will be understood by those of ordinary skill in the art that a surgical sealing tool may incorporate any combination of the above-described embodiments. In particular, haptic feedback may include combinations of signals in the form of a spatial haptic texture or a combined kinesthetic-vibrotactile stimulus. In addition, a single processor of a surgical sealing tool including one or more of the above-described embodiments may be configured to receive input/measurements from various sensor devices and perform the required tasks or calculations thereon.

As described herein, a pulsing vibrotactile alert or error may be utilized in various situations to indicate improper use of tool 100. The vibrotactile error alert may be utilized to ensure compliance with all proper instructions for use of tool 100, including sensed improper uses as described herein or other programmable improper uses such as time periods or sequence of steps. In one embodiment, the vibrotactile error haptic effect may be the same for all error states but may include a follow-on haptic, audible, or visual effect that will provide more information about the specific error state to users. These follow on effects could include additional haptic pulses with user discernable envelopes to indicate different conditions. Alternately, the error effect could be displayed with different temporal spacing depending on the severity of the condition. In another embodiment, the positive or negative valence alerts may be played for a fixed duration following the alert condition, which in some circumstances may continue past the time when the knife has returned to its resting position.

Figure 8:
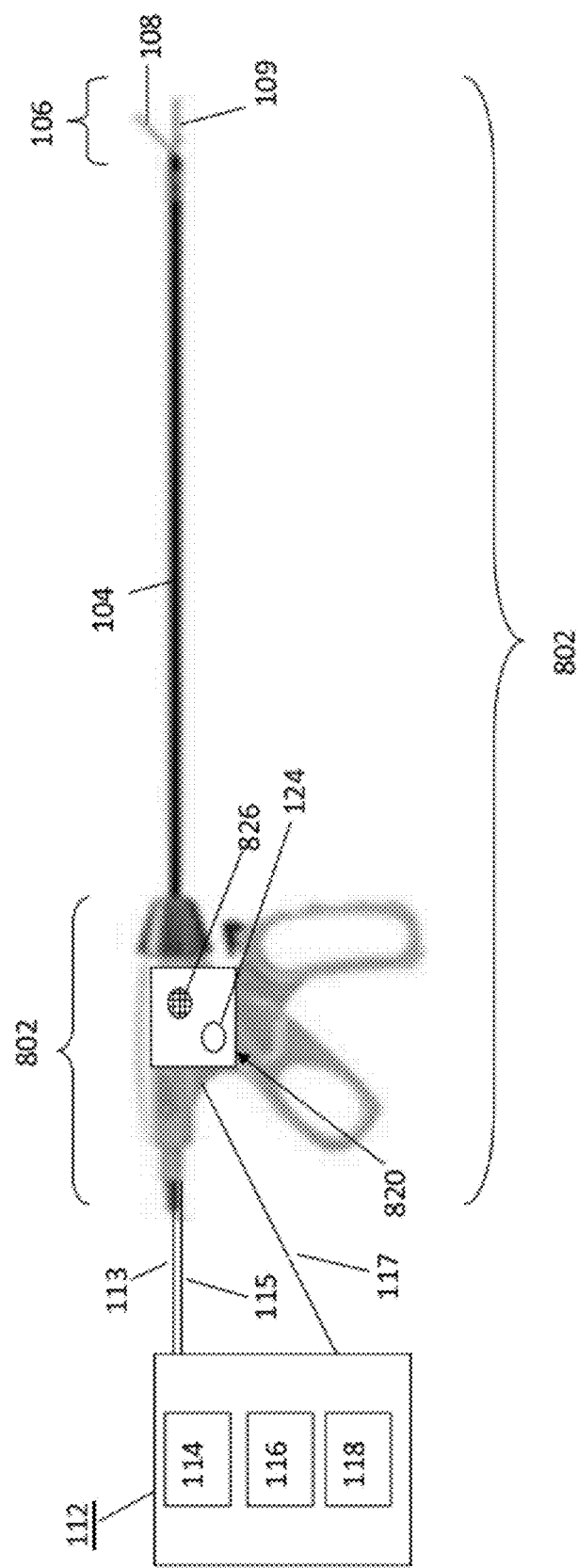
FIG. 8 is a diagram illustrating a side view of a surgical tool system having haptic and audio feedback mechanisms, according to an embodiment hereof.

For example, referring to FIG. 8, an embodiment incorporating two types or modes of feedback for the operator is shown. Specifically, haptic feedback system 820 provides both haptic and audio feedback via haptic actuator 124 and an audio device or speaker 826. Tactile mapping logic 118 communicates the processed information to one or more of haptic actuator 124 and audio device 826 according to which ones of these feedback mechanisms are enabled and how they are controlled to provide their respective outputs. In one embodiment, feedback may be provided to the operator in a continuous manner as the operator performs the surgery. In another embodiment, feedback may be provided to the operator as an alert to notify or warn the operator when a particular condition is satisfied. Further, one type of feedback (i.e., haptic or audio) may be provided in a continuous manner while another type of feedback is provided as an alert. In addition, haptic feedback alerts may augment continuous haptic feedback. In one embodiment, innocuous audible feedback may be utilized to indicate normal operation, tactile/haptic feedback may be utilized as an alert or warning to indicate to the user when a particular condition or state exists, and audible and/or visual feedback such as a beep and a flashing light may be utilized as an alarm to indicate to the user when a serious condition or state exists.

Figure 9:
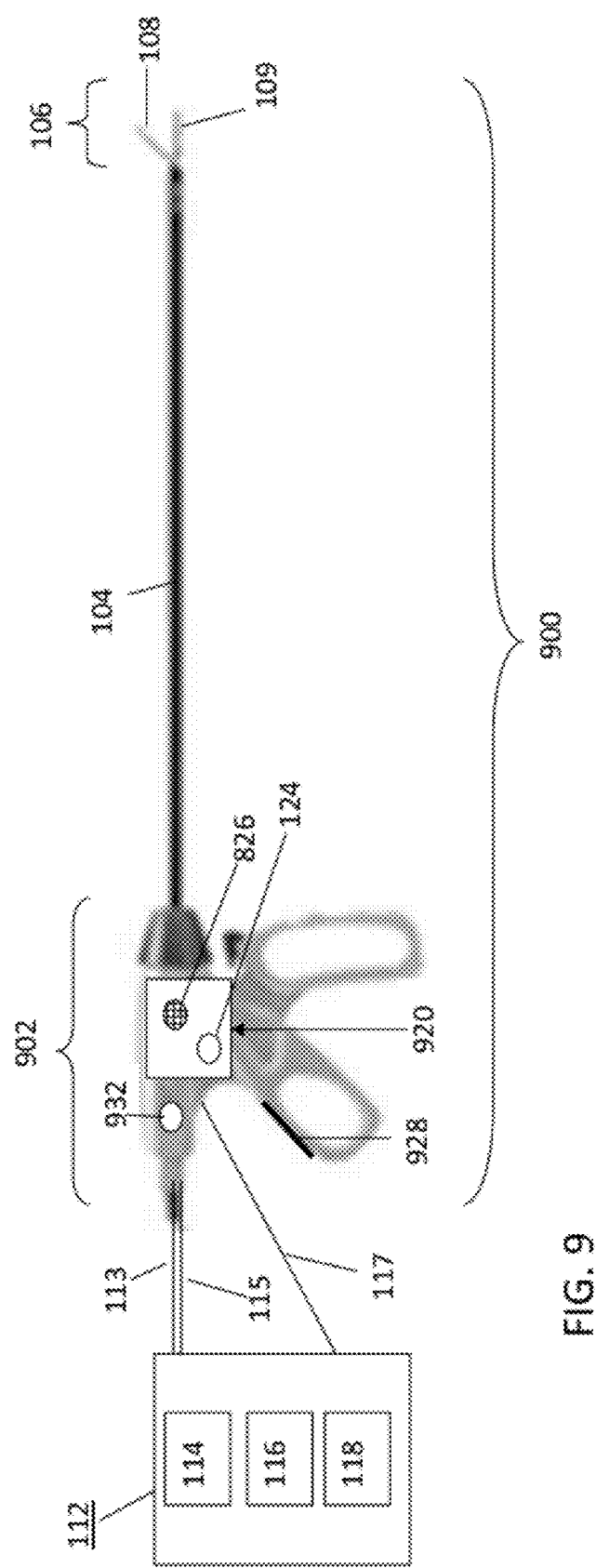
FIG. 9 is a diagram illustrating a side view of a surgical tool system having haptic, audio, and visual feedback mechanisms, according to another embodiment hereof.

Referring to FIG. 9, an embodiment incorporating three types or modes of feedback for the operator is shown. Specifically, haptic feedback system 920 provides haptic, audio, and visual feedback via haptic actuator 124, audio device or speaker 826, and visual display 928, respectively. Tactile mapping logic 118 communicates the processed information to one or more of haptic actuator 124, audio device 826, visual display 928 according to which ones of these feedback mechanisms are enabled and how they are controlled to provide their respective outputs. In this embodiment, visual display 928 is a liquid crystal display (LCD) screen on a back region of handle 102. In another embodiment, visual display 1128 may be incorporated into the camera monitor display of the laparoscope so that the visual feedback is always within the user's line or sight. Visual display 928 may be used to display impedance information and/or the operating status of RF power source 114. In one embodiment, an ultrasound transducer (not shown) may be coupled to distal portion 106 of tool 100 and visual display 928 may be configured to show ultrasound image information to assist the surgeon to position the tool as needed. Visual display 928 can include a touch screen, which can be configured to present information to the operator and can also be configured to sense when the operator presses certain portions of the touch screen. In this way, the touch screen can act as a touchable user interface with graphical presentation capabilities. Visual display 928 may include a graphical user device that enables the surgeon to select different feedback profiles, adjust sensor behavior, modify supplemental information, and the like.

According to the embodiment of FIG. 9, handle portion 902 of surgical tool 900 may further include one or more buttons 932. Buttons 932 can be configured using any suitable mechanism for allowing an operator to control the nature of the feedback that is provided to the operator. Buttons 932 may include devices for allowing certain levels, intensities, or amplitudes to be adjusted or certain selections to be made regarding the output presented to the operator. In some embodiments, buttons 932 may be configured as switches, such as momentary toggle switches, allowing an operator to select different ways in which sensor information is mapped or provided to respective output devices. Buttons 932 can be implemented as a rocker switch or as a one-dimensional control surface. According to one function of buttons 932, the operator can enable or disable one or more output mechanisms by controlling whether or not output signals based on the sensed signals are provided to the respective output devices. Another function of buttons 932 includes the ability to enable one or more output mechanisms. In this regard, the operator can control if and how feedback is presented in a visual, auditory, and/or haptic fashion. With feedback tailored to the surgeon's preferences, the tool can provide feedback to supplement the operator experience for better operation and performance.

It will be apparent to those of ordinary skill in the art that embodiments hereof relate to any type of tools that can be manipulated by an operator. More particularly, the tools described in the present disclosure include a handle portion that mechanically controls a distal portion of the tool. According to embodiments hereof, one or more sensor(s) located on the surgical tool and a haptic feedback system may collectively function to extract pertinent information regarding the operating status of the tool that is subsequently communicated to the operator as haptic, audio, and/or visual feedback. Although embodiments disclosed are tools for laparoscopic surgery, other embodiments can be used for non-laparoscopic surgeries such as in vascular or other catheterization where information detected from a sensor on the tool-tip can be communicated back to the catheter handle. Further, for endoscopy procedures, information detected from a sensor on a flexible endoscope can be communicated back to the endoscope handle. Other embodiments can be used for telesurgery or telepresence in order to, for example, perform routine external examinations and/or utilize open surgical tools by a remote doctor. Another embodiment is the inclusion of this type of feedback in robotic surgical systems, such as the da Vinci® Surgical System of Intuitive Surgical, Inc., to enable operators to have direct tactile feedback.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A surgical tool system comprising:
   an electrosurgical tool configured to seal tissue, the tool including a distal portion including a tissue sealing mechanism connected to a handle via a shaft;
   a sensor coupled to the electrosurgical tool, wherein the sensor is configured to monitor a tissue property;
   a control system electrically connected to the sensor, wherein the control system calculates sensor information from signals received from the sensor and processes the sensor information into signal commands;
   a feedback system including one or more haptic actuators coupled to the handle and electrically connected to the control system, wherein the control system communicates the signal commands to the feedback system and the feedback system uses the signal commands to generate haptic feedback relating to the sensor information to the handle;
a deployable cutting element on the distal portion of the tool and a displacement sensor coupled to the cutting element, wherein the haptic feedback generated by the feedback system also informs the user of whether the tissue is ready to be cut by the cutting element or the cutting speed of the cutting element; and
a trigger coupled to the deployable cutting element, wherein the one or more haptic actuators include a kinesthetic actuator coupled to the trigger to enable variable resistance to motion as the haptic feedback.

2. The surgical tool system of claim 1, wherein the sensor is configured to monitor an electrical tissue property and the haptic feedback generated by the feedback system informs a user that tissue is completely sealed.

3. The surgical tool system of claim 2, wherein the sensor is an impedance sensor coupled to the distal portion of the electrosurgical tool.

4. The surgical tool system of claim 1, wherein the sensor includes a first force sensor coupled to the handle and a second displacement sensor coupled to two opposing jaw members coupled to the distal portion of the tool and the haptic feedback generated by the feedback system informs a user of the thickness of tissue located within the two opposing jaw members coupled to the distal portion of the tool.

5. The surgical tool system of claim 1, wherein the tissue is a blood vessel and wherein the sensor is coupled to the distal portion of the tool and is selected from the group consisting of a pressure sensor and a displacement sensor, and the haptic feedback generated by the feedback system informs a user that the blood vessel is only partially located within two opposing jaw members coupled to the distal portion of the tool.

6. The surgical tool system of claim 1, wherein the haptic feedback generated by the feedback system also informs a user to the operating status of a power source that is electrically coupled to the electrosurgical tool.

7. The surgical tool system of claim 1, wherein the haptic feedback generated by the feedback system includes at least vibratory or kinesthetic feedback.

8. A surgical tool system comprising:
an electrosurgical tool configured to seal tissue of a blood vessel, the tool including a distal portion including a tissue sealing mechanism connected to a handle via a shaft;
a sensor coupled to the electrosurgical tool, wherein the sensor is configured to monitor a tissue property;
a control system electrically connected to the sensor, wherein the control system calculates sensor information from signals received from the sensor and processes the sensor information into signal commands; and
a feedback system including one or more haptic actuators coupled to the handle and electrically connected to the control system, wherein the control system communicates the signal commands to the feedback system and the feedback system uses the signal commands to generate haptic feedback relating to the sensor information to the handle;
wherein the sensor is coupled to the distal portion of the tool and is selected from the group consisting of a pressure sensor and a displacement sensor, and wherein the haptic feedback generated by the feedback system informs a user that the tissue is completely sealed by detecting that there is no pulsation through the blood vessel.

9. The surgical tool system of claim 8, further comprising a deployable cutting element on the distal portion of the tool and a cutting element displacement sensor coupled to the cutting element, wherein the haptic feedback generated by the feedback system also informs the user of whether the tissue is ready to be cut by the cutting element or the cutting speed of the cutting element.

10. The surgical tool system of claim 9, wherein a trigger is coupled to the deployable cutting element and the one or more haptic actuators include a kinesthetic actuator coupled to the trigger to enable variable resistance to motion as the haptic feedback.

11. A surgical tool system comprising:
an electrosurgical tool configured to seal tissue, the tool including a distal portion including a tissue sealing mechanism connected to a handle via a shaft;
a sensor coupled to the electrosurgical tool, wherein the sensor is configured to monitor a tissue property;
a control system electrically connected to the sensor, wherein the control system calculates sensor information from signals received from the sensor and processes the sensor information into signal commands; and
a feedback system including one or more haptic actuators coupled to the handle and electrically connected to the control system, wherein the control system communicates the signal commands to the feedback system and the feedback system uses the signal commands to generate haptic feedback relating to the sensor information to the handle;
wherein the signal commands for generating haptic feedback are dependent upon a user's level of experience.

12. The surgical tool system of claim 11, wherein the control system include a training mode and an experienced mode, wherein the signal commands for generating haptic feedback in the training mode are different than the signal commands for generating haptic feedback in the experienced mode.

13. The surgical tool system of claim 12, further comprising:
a deployable cutting element on the distal portion of the tool and a displacement sensor coupled to the cutting element, wherein the haptic feedback generated by the feedback system also informs the user of whether the tissue is ready to be cut by the cutting element or the cutting speed of the cutting element; and
a trigger coupled to the deployable cutting element, wherein the one or more haptic actuators include a kinesthetic actuator coupled to the trigger to enable variable resistance to motion as the haptic feedback,
wherein in the training mode, when measurements from the displacement sensor indicate that the cutting element is in the cutting position, the kinesthetic actuator is configured to provide maximum resistance on the trigger for impedance values measured by the sensor less than a first predetermined value, zero resistance on the trigger for impedance values greater than a second predetermined value, and gradually decreased resistance on the trigger in a continuous or stepwise fashion for impedance values between the first predetermined value and the second predetermined value.

14. The surgical tool system of claim 13, wherein in the experienced mode, when measurements from the displacement sensor indicate that the cutting element is in the cutting position, the kinesthetic actuator is configured to provide a relatively small detent on the trigger at the beginning of the cutting portion of the stroke for impedance values less than the second predetermined value and zero resistance on the trigger for impedance values greater than the second predetermined value.

15. The surgical tool system of claim 14, wherein the first predetermined value is approximately 100 ohms and the second predetermined value is approximately 450 ohms.

* * * * *